US006492513B1

(12) United States Patent
Nishihara et al.

(10) Patent No.: US 6,492,513 B1
(45) Date of Patent: Dec. 10, 2002

(54) METHOD FOR SEPARATING ANALOGOUS ORGANIC COMPOUNDS

(75) Inventors: Yutaka Nishihara, Toyama (JP); Keiji Honda, Aichi (JP); Koji Mukai, Toyonaka (JP); Norihiro Hashimoto, Nagoya (JP); Hiroshi Hatanaka, Toyama (JP); Michio Yamashita, Tsukuba (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/926,611

(22) PCT Filed: May 19, 2000

(86) PCT No.: PCT/JP00/03251

§ 371 (c)(1),
(2), (4) Date: Nov. 26, 2001

(87) PCT Pub. No.: WO00/71546

PCT Pub. Date: Nov. 30, 2000

(30) Foreign Application Priority Data

May 25, 1999 (JP) ............................................. 11/145103

(51) Int. Cl.$^7$ ...................... C07D 498/16; C07D 491/16
(52) U.S. Cl. .................... 540/456; 546/90; 585/809; 585/810; 585/820; 585/829; 210/660; 210/690
(58) Field of Search ............................ 546/90; 585/809, 585/810, 820, 829; 210/660, 690; 540/456

(56) References Cited

U.S. PATENT DOCUMENTS

| 4,826,603 A | 5/1989 | Hayes ........................ 210/635 |
| 5,672,726 A | 9/1997 | Ryu et al. |

FOREIGN PATENT DOCUMENTS

| WO | WO 96/40758 | 12/1996 |
| WO | WO 99/03860 | 1/1999 |

OTHER PUBLICATIONS

Patent Abstracts of Japan, JP 06–185397, Jul. 5, 1994.
Derwent Abstract, AN 1975–18271W[11], JP 49–088801, Aug. 24. 1974.
S. Soeda et al, Chemical Abstract of Seibutsu Kogaku Kaishi, vol. 76, No. 9, pp. 389–397, "Studies on the Development of Tacrolimus Production", 1998.
Patent Abstracts of Japan, JP 6–185397, Jul. 5, 1994.
Derwent Abstract, AN 1975–18271W, JP 49–088801, Aug. 24, 1974.
S. Soeda, et al., Chemical Abstract of Seibutsu Kogaku Kaishi, vol. 76, No. 9, pp. 389–397, "Studies on the Development of Tacrolimus Production", 1998.

*Primary Examiner*—Evelyn Mei Huang
(74) *Attorney, Agent, or Firm*—Oblon, Spivak, McClelland, Maier & Neustadt, P.C.

(57) ABSTRACT

The present invention relates to a method for separating a lactone-containing high-molecular weight compound having an alkyl group as its side chain from a lactone-containing high-molecular weight compound having an alkenyl group as its side chain by using a sulfonic acid group-containing cation exchange resin pretreated with silver ions.

9 Claims, 1 Drawing Sheet

METHOD FOR SEPARATING ANALOGOUS ORGANIC COMPOUNDS

This application is a 371 of PCT/JP 00/03251, filed on May 9, 2000

TECHNICAL FIELD

The present invention relates to a method for separating analogous compounds, more particularly a method for separating a lactone-containing high-molecular weight compound having an alkyl group as its side chain from a lactone-containing high-molecular weight compound having an alkenyl group as its side chain by using a sulfonic acid group-containing strong cation exchange resin pretreated with silver ions.

BACKGROUND ART

It is conventionally known to use silver ions for separating cis-trans isomers of an unsaturated aliphatic acid having the same carbon number (*J. Chromatography*, 149(1978) 417-). However, it has not been found out yet how to effectively separate compounds which are slightly different in a part of molecular structure, e.g., a compound having an alkyl group as its side chain from a compound having an alkenyl group as its side chain. This is because such compounds have the same or almost the same carbon number and are similar to each other in physical properties such as solubility in and affinity to solvents.

DISCLOSURE OF INVENTION

The inventors of the present invention have made extensive studies for a method for effectively separating compounds resembling each other in physical properties without changing the compounds themselves. Unexpectedly, they have found a method for separating compounds resembling each other in physical properties, i.e., a lactone-containing high-molecular weight compound having an alkyl group as its side chain from a lactone-containing high-molecular weight compound having an alkenyl group as its side chain, the lactone-containing high-molecular weight compounds having a common basic chemical structure, by using a sulfonic acid group-containing strong cation exchange resin pretreated with silver ions.

As suitable examples of the sulfonic acid group-containing strong cation exchange resins, mentioned are a synthetic base or a base of a silicon gel, such as gel-type resins and porous resins which can be used with a polar solvent but cannot be used with a nonpolar solvent; and highly porous resins which can be used with both polar and nonpolar solvents. These resins may be selected according to the polarity of an eluent used.

The sulfonic acid group-containing strong cation exchange resin may be a benzenesulfonic acid group-containing strong cation exchange resin having benzenesulfonic acid groups at an end. For example, the resin may be a base of a copolymer of a styrene monomer and divinylbenzene (DVB), or a base of silica gel.

As examples of benzenesulfonic acid group-containing strong cation exchange resins, i.e., sulfonated copolymers of styrene monomer and DVB, mentioned are Diaion® (SK series, RCP series, HPK series, PK series such as PK 206) (trademark, produced by Mitsubishi Chemical Corporation, Japan), Amberlite® (IR120B, IR200) and Duolite® (C20, C26) (trademark, produced by Rohm & Haas Company), Dowex® (50W-X8, MSC-1) (trademark, produced by Dow Chemical Company), Ionac® (C-240) (trademark, produced by Sybron Chemicals Inc.) and lewatit® (S-100, SP series) (trademark, produced by Bayer Corporation).

As examples of benzenesulfonic acid group-containing strong cation exchange resins having silica gel as a base, mentioned are strong cation exchange resins coated with a benzenesulfonic acid group-containing silicone polymer such as Capcell Pak® (SCX series) (trademark produced by Shiseido Company Limited, Japan) whose base is coated with a thin film of silicone polymer and to which a sulfonic acid group at an end is then introduced.

Among these benzenesulfonic acid group-containing strong cation exchange resins, Diaion® (RCP series and PK series) and Capcell Pak® (SCX series) are particularly preferred.

The silver ion usable for pretreating the sulfonic acid group-containing strong cation exchange resin may preferably be provided from various silver salts which can produce silver ions in water, such as silver nitrate, silver perchlorate or the like.

The sulfonic acid group-containing strong cation exchange resin may be pretreated with the silver ion by passing an aqueous solution of the silver salt therethrough if the resin is of an H type, or if it is of an Na type, by changing it into the H type, washing with water, adjusted to pH 3 to 4 and passing an aqueous solution of the silver salt. This pretreatment with silver ions may preferably be carried out by charging the silver salt at 1 mol/L-R or higher.

The purification method of the present invention can be carried out by the following steps.

(i) The mixture, i.e., the crude substance to be separated, containing the "lactone-containing high-molecular weight compound having an alkyl group as its side chain" and the "lactone-containing high-molecular weight compound having an alkenyl group as its side chain" can be dissolved in a suitable solvent, such as acetone, etc, and be charged to the column chromatography filled with the sulfonic acid group-containing strong cation exchange resin pretreated with silver ions.

(ii) And, the elution can be carried out with a suitable eluent, such as acetone, a mixture of ethyl acetate and methyl alcohol, and so on.

Separation method using the sulfonic acid group-containing strong cation exchange resin pretreated with silver ions may be conducted by a fixed bed system or a continuous bed system. The fixed bed system includes a single bed system, a multiple bed system, a double bed system, a mixed bed system, an ion exchange filtration system, a circulatory system and the like, from the viewpoint of operational process. The fixed bed system includes a down flow regeneration system, an ascending flow regeneration system, a countercurrent ascending flow regeneration system, a countercurrent regeneration system, an ex-column regeneration system and the like, from the viewpoint of regeneration process. On the other hand, the continuous bed system includes a fluidized bed system (a countercurrent contacting system, a multistage batch system), a moving bed system (an ascending type (a single column type, a multiple column type), a descending type (a single column type, a multiple column type), a simulated moving-bed system, an endless belt system (a liquid-liquid extraction system)) and the like, among which the simulated moving-bed system is efficient and suitable for mass production.

The lactone-containing high-molecular weight compound to which the separation method of the present invention may be applicable means those having at least one lactone ring in their molecules and having a molecular weight of about 400 or more. They may be monocyclic, bicyclic, tricyclic or the like. More preferably, they are formed of 12 or more atoms. Such monocyclic compounds include erythromycins, leucomycins, methymycins and the like. Such tricyclic compounds include compounds having a lactone ring such as a tricyclic compound shown in EP0184162; hetero atoms-containing tricyclic compounds shown in EP0427680, EP0532088 or WO93/04680. And the most preferable one is 1,14-dihyroxy-12-[2-(4-hydroxy-3-methoxycyclohexyl)-1-methylvinyl]-23,25-dimethoxy-13,19,21,27-tetramethyl-11, 28-dioxa-4-azatricyclo[22.3.1.0$^{4,9}$]octacos-18-ene-2,3,10, 16-tetraone. And the most preferable position which is substituted by an alkyl or alkenyl group as the side chain is the 17-position thereof, and which is tacrolimus when the 17 position is substituted with allyl and ascomycin when it is substituted with ethyl. Further, rapamysins and the like are also exemplified as a suitable one.

As alkyl group(s) as the side chain of the lactone-containing high-molecular weight compound, mentioned are straight or branched alkyl groups having a carbon number of 1 to 6 such as methyl, ethyl, propyl, isopropyl, butyl, isobutyl, sec-butyl, tert-butyl, pentyl, isopentyl, hexyl and the like, among which preferred are those having a carbon number of 1 to 4 such as methyl, ethyl, propyl, isopropyl, butyl and isobutyl.

As alkenyl group(s) as the side chain of the lactone-containing high-molecular weight compound having the common basic chemical structure as the above-mentioned compound, mentioned are straight or branched alkenyl groups having a carbon number of 2 to 6 such as vinyl, propenyl (allyl or 1-propenyl), butenyl, isobutenyl, pentenyl, hexenyl and the like, among which vinyl and propenyl are preferred.

Preparation of a Substance to be Separated

A culture medium (100 mL) containing 1% of cornstarch, 1% of glycerin, 0.5% of glucose, 1% of cottonseed meal, 0.5% of dried yeast, 0.5% of corn steep liquor and 0.2% of calcium carbonate, adjusted to pH 6.5, was poured into eight 500 mL Erlenmeyer flasks and sterilized at 120° C. for 30 minutes. A loopful of slant culture of *Streptomyces tsukubaensis* No. 9993 (Deposit No. FERM BP-927 at the National Institute of Bioscience and Human Technolog, Agency of Industrial Science and Technology, Japan, under the Budapest Treaty) was inoculated to the medium in each of the flasks and cultured at 30° C. for 72 hours on a rotary shaker. This culture was transferred as a seed culture to 160L of the same medium which was contained in a 200 L jar-fermentor pre-sterilized at 120° C. for 30 minutes and to which 0.05% of Adekanol® (defoaming agent, trademark, produced by Asahi Denka Co., Japan) and 0.05% of silicone (produced by Shinetsu Chemical Co., Japan) had been added. This was pre-cultured at 30° C. for 48 hours with agitation at 200 rpm under aeration of 160 L/min. This pre-culture, 30 L, was inoculated to 3,000 L of a production medium of pH 6.8 pre-sterilized at 120° C. for 30 minutes containing 3% of soluble starch, 0.8% of wheat germ, 0.4% of dried yeast, 0.6% of corn steep liquor, 0.1% of calcium carbonate, 0.05% of Adekanol® and 0.05% of silicone in a 4 t tank, and was fermented at 25° C. for 168 hours with agitation at 140 rpm under aeration of 1,500 L/min.

The cultured broth thus obtained was filtered by using 50 kg of diatomaceous earth. Mycelial cakes were extracted with 1,000 L of acetone to give 1,000 L of extract. The acetone extract from the mycelial cakes and the filtrate (2,700 L) were combined and passed through a column of a non-ionic adsorption resin "Diaion HP-20" (trademark, produced by Mitsubishi Chemical Corporation, Japan) (200 L). After washing with 600 L of 50% aqueous acetone, elution was carried out with 75% aqueous acetone. The solvent in the eluate was removed by evaporation under reduced pressure to give 40 L of an aqueous residue. The residue was extracted with 40 L of ethyl acetate twice. The ethyl acetate extract was concentrated under reduced pressure to give an oily residue. The oily residue was dissolved in a mixture of n-hexane and ethyl acetate (1:1, v/v, 3 L) and subjected to column chromatography using 70 L of silica gel (produced by Merck & Co., Ltd. 70–230 mesh) packed with the same solvent.

Elution was carried out successively with a mixture of n-hexane and ethyl acetate (1:1, v/v, 420 L and 1:2, v/v, 420 L), 210 L of ethyl acetate and then 210 L of acetone. Fractions were collected at elution volume from 350 L to 420 L (first eluate), from 490 L to 840 L (second eluate) and from 980 L to 1,190 L (third eluate). The second eluate was concentrated under reduced pressure, and acetone was added to replace the solvent (50 mg/mL). Thus crude substance to be separated by column chromatography was obtained.

BEST MODE FOR CARRYING OUT THE INVENTION

The following Examples are given only for the purpose of illustrating the present invention in more detail.

EXAMPLE 1

Separation by Column Chromatography using Diaion® RCP160M (Trademark, Produced by Mitsubishi Chemical Corporation, Japan)

(1) Treatment of Diaion® RCP160M, an ion Exchange Resin, with a Silver Salt 1M aqueous silver nitrate solution (3 column volume) was passed through Diaion® RCP160M (H+type), which was then washed with water (4 column volume) to remove an excess of silver nitrate. The ion exchange resin was equilibrated with methanol (4 column volume) and then with a mixture of ethyl acetate and methanol (1:1).

(2) Separation Test Using a Single Column

Figure 1:
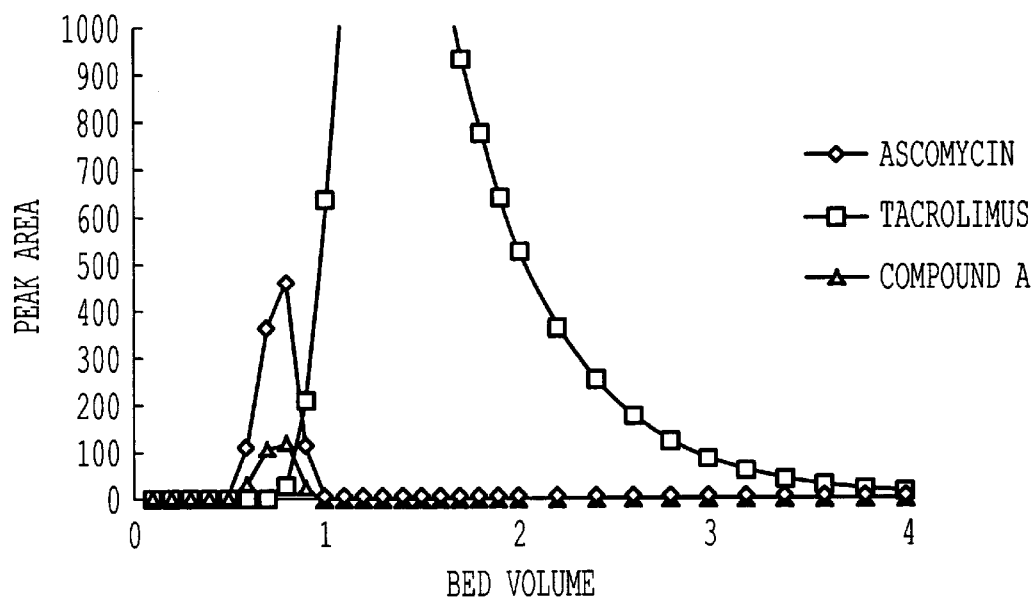
FIG. 1 is a chart showing separation by column chromatography using Diaion® RCP160M pretreated with silver ions.

The crude substance to be separated by column chromatography obtained as described above was subjected to column chromatography using Diaion® RCP160M treated with the aqueous silver nitrate solution. Separation was carried out using a column of 20 mm φ×500 mH (425 μm) (150 mL) and a mixture of ethyl acetate and methanol (1:1) as an eluent at a load of 10 g/L-R in terms of tacrolimus, a flow rate sv=1 and a temperature of 30° C. The obtained separation pattern is shown in FIG. 1.

Tacrolimus, ascomycin and 17-propyl-1,14-dihydroxy-12-[2-(4-hydroxy-3-methoxycyclohexyl)-1-methylvinyl]-23, 25-dimethoxy-13,19,21,27-tetramethyl-11,28-dioxa-4-azatricyclo-[22.3. 1.0$^{4,9}$]octacos-18-ene-2,3,10,16-tetraone (referred to as Compound A hereinafter) were isolated and identified.

EXAMPLE 2

Separation by Column Chromatography Using Capcell Pak® SCX UG80 (Trademark, Produced by Shiseido Company Limited, Japan)

(1) Separation Test Using a Single Column

Figure 2:
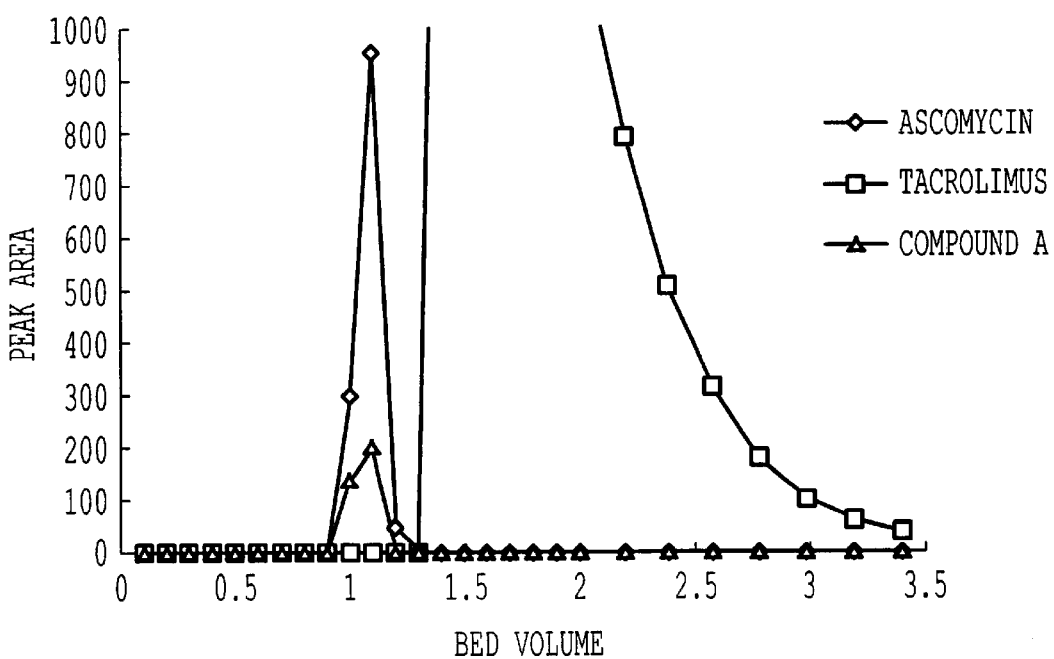
FIG. 2 is a chart showing separation by column chromatography using Capcell Pak® SCX pretreated with silver ions.

The crude substance to be separated by column chromatography obtained in the same manner as in Example 1 was subjected to column chromatography using Capcell Pak® SCX UG80 exchanged with silver ions. Separation and purification was carried out by using a column of 20 mm φ×250 mH (20 μm) (78 mL) and acetone as an eluent at a load of 5 g/L-R in terms of tacrolimus, a flow rate sv=1.5 and 30° C. The obtained separation pattern is shown in FIG. 2.

(2) Continuous Separation by a Small-sized Simulated Moving-bed Device

The crude substance to be separated by column chromatography obtained as described above was subjected to separation by a small-sized simulated moving-bed device (produced by Organo Corporation, Japan, a small-sized new JO system chromatographic separator, TREZONE®) provided with Capcell Pak® SCX UG80 treated with an aqueous solution of silver nitrate. Separation and purification was carried out under the following conditions; eluent—acetone; charge concentration—25 g/L; charging method—24 g/cycle×4 cycles; column—(20 μm) of 2.26 L (280 mL×8); the sum of loads—42 g/L-R (a batch load); amount of liquid in an active fraction—1.5 L/cycle (with respect to 0.65 column volume); and temperature—20° C. The purity of each substance in the active fraction was determined by the HPLC analysis. The results are shown in Table 1.

TABLE 1

|  | Purity in the Crude Substance (%) | Purity in the Eluted Fraction (%) |
|---|---|---|
| tacrolimus | 85.4 | 92.7 |
| ascomycin | 5.45 | 0.11 |
| Compound A | 1.30 | n.d. | n.d.: not detectable

INDUSTRIAL APPLICABILITY

Unexpected effect in separation was obtained by applying the sulfonic acid group-containing strong cation exchange resin pretreated with silver ions to the separation of the lactone-containing high-molecular weight compound having an alkyl group as a side chain from that having an alkenyl group as a side chain.

The separation method of the present invention is quite useful because of its repeatability, a large-scale applicability and/or its economical benefit. Therefore, the present invention is applicable to a chemical industry, particularly a pharmaceutical industry, in which the mass-production and the purity of the objected compounds are critical.

What is claimed is:

1. A method for separating a lactone-containing high-molecular weight compound having an alkyl group as its side chain from a lactone-containing high-molecular weight compound having an alkenyl group as its side chain, said lactone-containing high-molecular weight compounds having a common basic chemical structure, by using a sulfonic acid group-containing cation exchange resin treated with silver ions, wherein said common basic chemical structure of the lactone-containing high-molecular weight compounds is 1,14-dihydroxy-12-[2-(4-hydroxy-3-methoxycyclohexyl)-1-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone.

2. The method of claim 1, wherein said alkyl group and said alkenyl group as the side chain are each substituted at the 17-position of said common basic chemical structure.

3. The method of claim 1, wherein said alkyl group is ethyl or propyl and said alkenyl group is propenyl.

4. The method of claim 1, wherein said silver ions are provided from silver salts.

5. The method of claim 1, wherein the separation is conducted by using a simulated moving-bed system.

6. The method of claim 1, wherein said sulfonic acid group-containing cation exchange resin is a benzensulfonic acid group-containing cation exchange resin.

7. The method of claim 6, wherein the base resin is formed of a copolymer of styrene monomer and divinylbenzene, or a silica gel coated with a thin film of silicone polymer.

8. The method of claim 1, wherein said alkenyl group is allyl.

9. The method of claim 1, wherein the lactone-containing high-molecular weight compounds to be separated are selected from the group consisting of tacrolimus and ascomycin.

* * * * *